(12) United States Patent
Kimura (10) Patent No.: US 8,679,000 B2
(45) Date of Patent: Mar. 25, 2014

(54) ENDOSCOPE HAVING SIGNAL CABLE

(75) Inventor: Soichiro Kimura, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 120 days.

(21) Appl. No.: 13/360,596

(22) Filed: Jan. 27, 2012

(65) Prior Publication Data

US 2012/0220825 A1  Aug. 30, 2012

(30) Foreign Application Priority Data

Feb. 24, 2011 (JP) ................................. 2011-038181

(51) Int. Cl.
*A61B 1/04* (2006.01)

(52) U.S. Cl.
USPC ........................................................ 600/110

(58) Field of Classification Search
USPC ........................................ 600/109, 110, 129
See application file for complete search history.

(56) References Cited

U.S. PATENT DOCUMENTS

| | | | | |
|---|---|---|---|---|
| 4,677,471 A | * | 6/1987 | Takamura et al. | 348/76 |
| 4,831,456 A | | 5/1989 | Takamura | |
| 4,832,003 A | * | 5/1989 | Yabe | 600/109 |
| 4,993,405 A | * | 2/1991 | Takamura et al. | 600/110 |
| 5,454,366 A | * | 10/1995 | Ito et al. | 600/109 |
| 6,595,913 B2 | * | 7/2003 | Takahashi | 600/110 |
| RE43,281 E | * | 3/2012 | Higuma et al. | 600/133 |
| 2009/0177038 A1 | | 7/2009 | Yashiro et al. | |
| 2011/0245608 A1 | * | 10/2011 | Takahashi et al. | 600/109 |

FOREIGN PATENT DOCUMENTS

| | | |
|---|---|---|
| JP | 05-261064 A | 10/1993 |
| JP | 09-146011 A | 6/1997 |
| JP | 2008-118568 A | 5/2008 |

OTHER PUBLICATIONS

European Search Report dated Jun. 19, 2012.

* cited by examiner

*Primary Examiner* — Philip R Smith
(74) *Attorney, Agent, or Firm* — McGinn IP Law Group, PLLC (57) ABSTRACT

An endoscope has a section of an elongated tube for entry in a body cavity. An end shell is disposed at a distal end of the elongated tube. An imaging window area is formed in the end shell. A lens barrel is secured to the end shell, and aligned with the imaging window area. An imaging device photoelectrically detects object light from the lens barrel. A circuit board has the imaging device mounted thereon. A signal cable has a cover material, and plural filaments covered by the cover material, and connected to the circuit board. A cable retaining device partially retains the cover material fixedly. A tip portion is formed at a distal end of the cable retaining device. A coupling device keeps the tip portion laterally movable on the end shell, to prevent stress in the cable retaining device from exertion to the end shell.

13 Claims, 7 Drawing Sheets

ENDOSCOPE HAVING SIGNAL CABLE

BACKGROUND OF THE INVENTION

1. Field of the Invention

The present invention relates to an endoscope having a signal cable. More particularly, the present invention relates to an endoscope in which various circuit elements and parts can be protected from damages even when a signal cable is pulled abruptly or forcibly, and which can have a simplified structure.

2. Description Related to the Prior Art

An endoscope has a section of an elongated tube for entry in a body cavity of a patient. The elongated tube includes a head assembly with a rigid tip, a steering device and a flexible device arranged in a proximal direction. A distal surface of the head assembly includes an imaging window, lighting window, distal instrument opening, end nozzle and the like. A solid state imaging unit is disposed on an inner surface of the head assembly, and positioned at the imaging window. A light guide device is disposed on the inner surface of the head assembly, and positioned at the lighting window. The steering device is constituted by plural link elements connected with one another. Wires of the steering device are pulled to bend the head assembly in a desired direction. The flexible device has such a length as 1-2 meters for reach of the head assembly to an object of interest in a body cavity.

The solid state imaging unit includes a lens system and an imaging device. The lens system includes a lens, prism and other optical elements. The imaging device is a CCD or other image sensor for photoelectrically converting image light focused by the lens system into an image signal. There are a flexible circuit board and an additional circuit board. A signal cable connects the imaging device to the flexible circuit board and the additional circuit board. Electronic circuit elements are mounted on the flexible and additional circuit boards for driving the imaging device. A processing apparatus is connected by the signal cable to the flexible and additional circuit boards, and supplied with a signal from the solid state imaging unit. The processing apparatus processes the signal in the image processing, and drives a monitor display panel to display an image of an object of the body cavity, for example a lesion of tissue.

The signal cable from the solid state imaging unit to the processing apparatus is a multi-core cable. As the signal cable extends for a full length of the elongated tube, the signal cable is pushed and pulled at each time that the elongated tube is looped, steered or otherwise bent. There are connecting portions where the signal cable is connected to the flexible circuit board. Stress of the push and pull may drop the signal cable from the connecting portions.

Various suggestions have been made for preventing drop of the signal cable. JP-A 5-261064 discloses the endoscope in which the signal cable is soldered to one end of the flexible circuit board. The flexible circuit board is bent in a channel shape to extend around a soldered portion of the signal cable. A shield tape and insulation tape are used to cover the flexible circuit board. Adhesive agent is filled in an inner space of the flexible circuit board and prevents deformation by hardening. The endoscope includes a circuit board and a support sleeve or connection sleeve. The circuit board has a portion where the signal cable is attached, and is fixedly secured to the support sleeve by use of a spacer plate and a screw. Even when the signal cable is pulled strongly, the circuit board does not move. Stress of distortion or inclination exerted by the signal cable to the circuit board is not transmitted to the imaging device or the lens system, because absorbed by the circuit board with flexibility.

JP-A 9-146011 discloses the solid state imaging unit in which encapsulant is used to encapsulate the connecting portions between the flexible circuit board and the signal cable.

JP-A 2008-118568 discloses the solid state imaging unit in which a rigid housing or reinforcing frame contains the imaging device and a portion of the flexible circuit board for mounting circuit elements. The adhesive agent is filled in an inner space of the processing apparatus. A thermal contraction tube is used to cover the rigid housing and a tip of the signal cable soldered on the flexible circuit board. An inner space of the thermal contraction tube is filled with the adhesive agent for sealing tightly.

In the solid state imaging unit of JP-A 5-261064, there is a shortcoming in complicated handling for attaching the circuit board to the support sleeve with the screw. In the solid state imaging unit of JP-A 9-146011, stress of push and pull in the signal cable is transmitted to the flexible circuit board or the connecting portions of the flexible circuit board. The connecting portions of soldering between the signal cable and the flexible circuit board or the connecting portions between the flexible circuit board and the imaging device may receive stress applied to the flexible circuit board. It is likely that peeling or breakage may occur in a weak portion of any one of those elements.

According to the solid state imaging unit of JP-A 2008-118568, a size of the rigid housing must be predetermined according to a size of the imaging device, as the imaging device is contained in the rigid housing. Various elements including the imaging device and others associated therewith are technically complicated in compliance with requirement for the endoscope, for example high definition, reduction of a diameter, use with an autoclave system, and the like. If the size of the endoscope is enlarged with a larger number of functions of the imaging device and other elements, the size of the rigid housing for containment will be enlarged. A diameter of the head assembly of the elongated tube will be larger. There will arise a problem in that physical stress of a patient will be high in use of the endoscope.

SUMMARY OF THE INVENTION

In view of the foregoing problems, an object of the present invention is to provide an endoscope in which various circuit elements and parts can be protected from damages even when a signal cable is pulled abruptly or forcibly, and which can have a simplified structure.

In order to achieve the above and other objects and advantages of this invention, an endoscope having a section of an elongated tube for entry in a body cavity is provided, and includes an end shell disposed at a distal end of the elongated tube. An imaging window area is formed in the end shell. A lens barrel is secured to the end shell, and aligned with the imaging window area. An imaging device photoelectrically converts object light from the lens barrel. A circuit board has the imaging device mounted thereon. A signal cable has plural filaments for transmitting at least an image signal from the imaging device, and a cover material for covering the filaments. A cable holder includes a cable retaining device and a tip portion, the cable retaining device partially anchoring the cover material of the signal cable, the tip portion being disposed on a distal side of the cable retaining device. A coupling device keeps the tip portion laterally movable on the end shell, to prevent stress in the cable retaining device from exertion to the end shell.

Furthermore, amount hole is formed through the end shell, for contacting and receiving the lens barrel therein.

The tip portion is in a plate shape.

Furthermore, a shell wall is formed with the end shell, and disposed outside the tip portion in the radial direction of the elongated tube. A receiving opening is formed in an inner surface of the shell wall, for receiving the tip portion. A neck section is formed locally with the tip portion with a width decreased in a transverse direction of the tip portion. The coupling device includes a receiving projection, disposed to project from an edge of the receiving opening, engaged with the neck section, for keeping the tip portion movable inside the receiving opening.

The receiving opening has a larger size than the tip portion in the transverse direction and the radial direction.

The receiving opening includes a regulating surface for receiving contact of an end of the tip portion upon lateral movement of the cable holder.

Furthermore, a support sleeve supports the end shell at a distal end thereof, to cover the receiving opening.

Furthermore, a prism directs the object light from the lens barrel to the imaging device.

Furthermore, an additional circuit board has a circuit element other than the imaging device mounted thereon, and including first and second contact points, the first contact point being connected with the circuit board, the second contact point being connected with the signal cable.

The cable holder further includes a cover device, disposed to extend in the axial direction between the cable retaining device and the tip portion, for partially containing the filaments.

The cover device includes a center wall, and side walls disposed to project from edges of the center wall in a U shape as viewed in the axial direction.

The cable holder has a cross-sectional area decreasing in the axial direction toward a proximal side, and offsets an axis of the signal cable from an optical axis of the lens barrel in the end shell.

The cable retaining device includes a center plate, and an anchoring portion for partially retaining the signal cable on the center plate.

The anchoring portion includes first and second side projections, disposed to project laterally from the center plate, for squeezing the signal cable.

The anchoring portion is a winding material. Furthermore, sealant material or adhesive agent attaches the winding material to the center plate and the signal cable.

The additional circuit board is at least partially opposed to a wall of the tip portion.

The cable retaining device includes a center plate having a small width. First and second pairs of projections are disposed respectively in a channel shape, the first pair being disposed on a distal side of the center plate, the second pair being disposed on a proximal side of the center plate.

Furthermore, a winding material is wound around the center plate and the cover material of the signal cable. A sealant material is disposed around the winding material.

Also, an endoscope having a section of an elongated tube for entry in a body cavity is provided, and includes an end shell disposed at a distal end of the elongated tube. An imaging window area is formed in the end shell. A lens barrel is secured to the end shell, and aligned with the imaging window area. An imaging device photoelectrically detects object light from the lens barrel. A circuit board has the imaging device mounted thereon. A signal cable has plural filaments and a cover material for covering the filaments, the filaments being connected to the circuit board. A cable retaining device partially anchors the cover material of the signal cable. A tip portion is formed at a distal end of the cable retaining device in an axial direction of the elongated tube. A coupling device keeps the tip portion laterally movable on the end shell, to prevent stress in the cable retaining device from exertion to the end shell.

Accordingly, various circuit elements and parts can be protected from damages even when a signal cable is pulled abruptly or forcibly, and the endoscope can have a simplified structure, because the tip portion is received by the receiving device in a pivotally movable manner.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1:
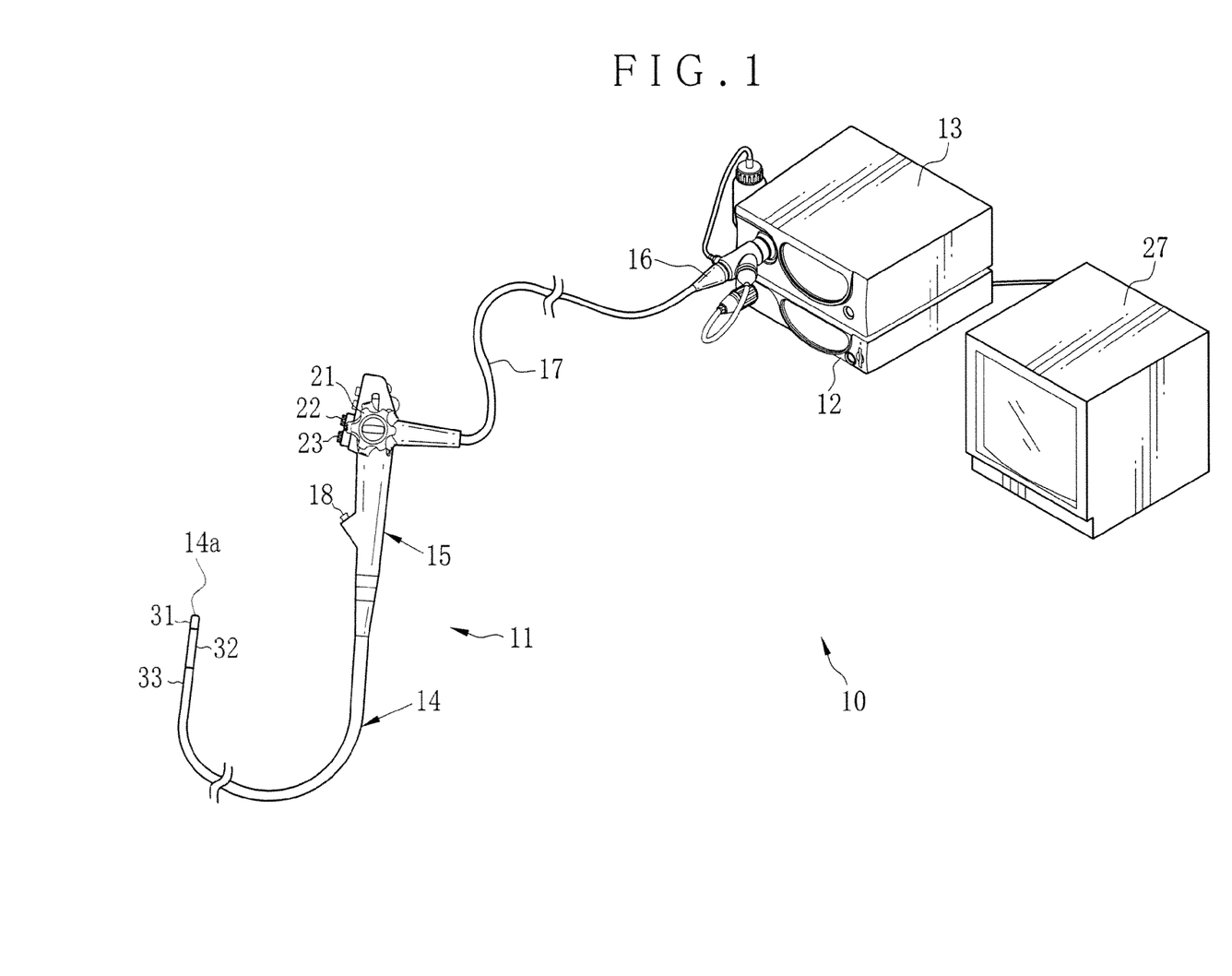
FIG. 1 is a perspective view illustrating an endoscope system.

In FIG. 1, an electronic endoscope system 10 includes an endoscope 11, a processing apparatus 12 and a light source apparatus 13. The endoscope 11 includes a section of a flexible elongated tube 14, a handle device 15, a connector 16 and a universal cable 17. The elongated tube 14 is for entry in a body cavity, such as a gastrointestinal tract, of a patient. The handle device 15 is disposed at a proximal end of the elongated tube 14. The connector 16 is used for connection to the processing apparatus 12 and the light source apparatus 13. The universal cable 17 is used for connection between the handle device 15 and the connector 16.

Figure 2:
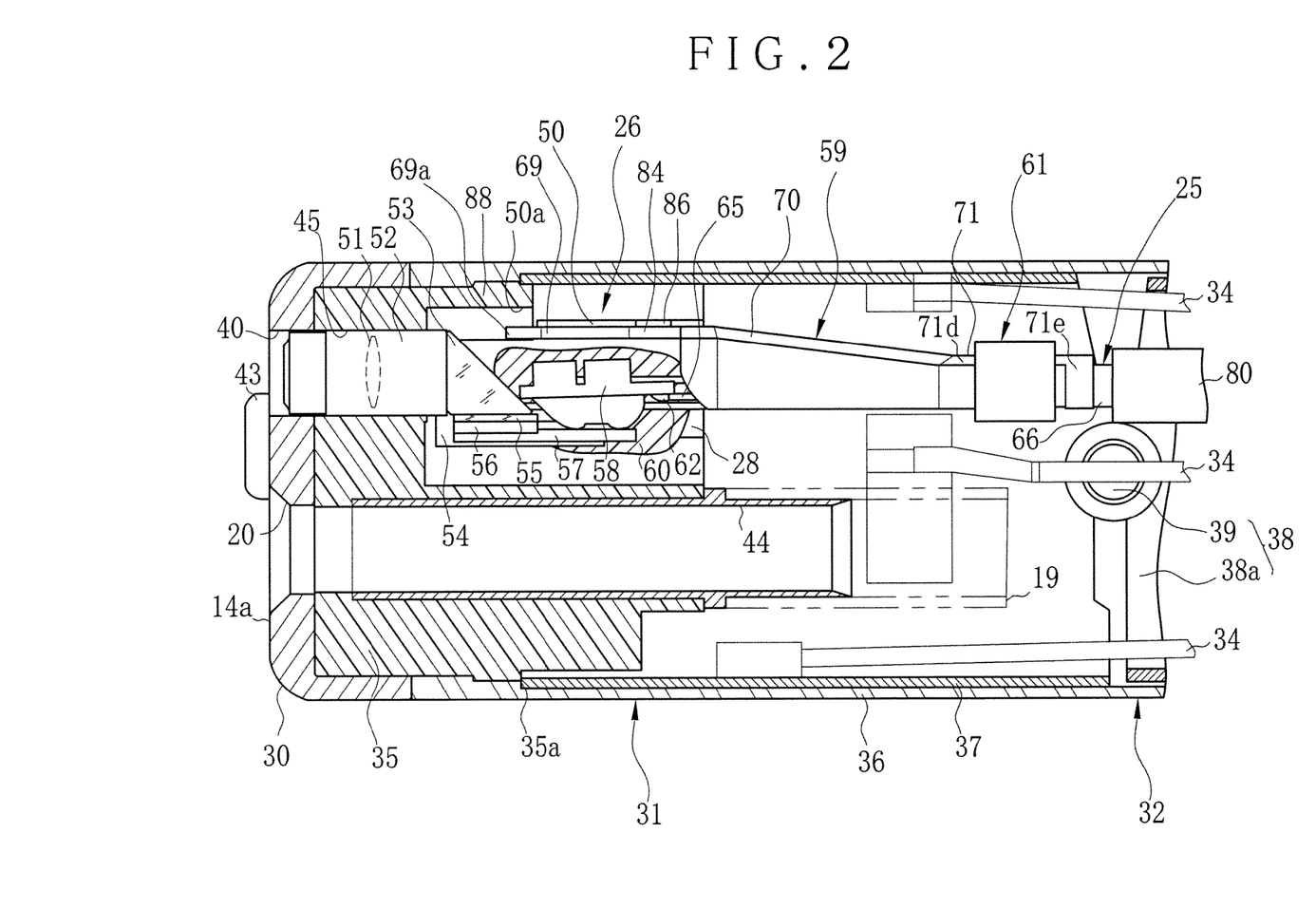
FIG. 2 is a vertical section illustrating a head assembly of an endoscope.

A proximal instrument opening 18 is formed at a distal portion of the handle device 15. The proximal instrument opening 18 is used for entry of a medical instrument, such as a forceps, electrocautery device and the like. An instrument channel 19 of FIG. 2 is formed through the elongated tube 14. A distal instrument opening 20 is formed in a distal surface 14a of the elongated tube 14. The proximal instrument opening 18 opens at a proximal end of the instrument channel 19 which extends to the distal instrument opening 20.

Figure 3:
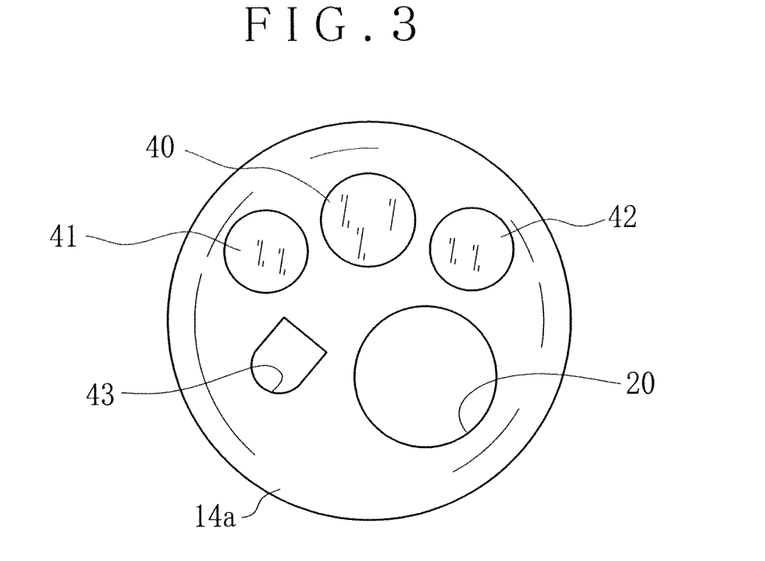
FIG. 3 is a front elevation illustrating a distal surface of a section of an elongated tube.

The handle device 15 includes steering wheels 21, a fluid supply button 22, a suction button 23 and a release button. A head assembly 31 of the elongated tube 14 is steered up and down and to the right and left by operating the steering wheels 21. An end nozzle 43 of FIG. 3 is formed to eject air or water upon depression of the fluid supply button 22. When the suction button is depressed, body fluid is sucked through the distal instrument opening 20, such as blood, particles of tissue or the like. The release button is provided in the handle device 15, and operable for recording a still image of the body part.

The processing apparatus 12 is connected to the light source apparatus 13 electrically, and controls various functions of the endoscope system 10. In FIG. 2, a signal cable 25 is disposed to extend within the universal cable 17 and the elongated tube 14, and supplies power to the endoscope 11. A solid state imaging unit 26 is incorporated in the head assembly 31 and is controlled by the processing apparatus 12. Also, the processing apparatus 12 receives a signal from the solid state imaging unit 26 through the signal cable 25, and produces image data by processing of various functions. A monitor display panel 27 is connected to the processing apparatus 12. The display panel 27 displays an image according to the image data from the processing apparatus 12.

The elongated tube 14 includes the head assembly 31, a steering device 32 and a flexible device 33 arranged in a proximal direction from the distal surface 14a. In FIG. 2, the head assembly 31 includes an end shell 35 or distal housing or head assembly housing, and a cover tube 36. The end shell 35 is formed from hard resin. An end cap 30 or cover is formed from soft resin, and fitted on the end shell 35. The steering device 32 has a support sleeve 37 of metal on a distal side. The cover tube 36 covers the end shell 35 and the support sleeve 37 to constitute the head assembly 31. The steering device 32 has a link train 38 and the support sleeve 37. The link train 38 includes a plurality of link elements 38a and pins 39 for connecting the link elements 38a with one another. The steering device 32 is steered by turn of its portion connected with the pins 39 at a predetermined angle. Four wires 34 are extended within the steering device 32 from the steering wheels 21 of the handle device 15 in FIG. 1. When the steering wheels 21 are rotated, the wires 34 are moved in the proximal or distal direction. Thus, the steering device 32 is steered in the vertical or horizontal direction at a desired angle. The head assembly 31 is oriented in a desired direction in a body cavity, to image an object of a body part with the solid state imaging unit 26. The flexible device 33 extends flexibly between the handle device 15 and the steering device 32 with a small diameter.

The end shell 35 is cylindrical, and formed from hard resin. A step wall 35a is formed on the outside of the end shell 35. The end cap 30 is fitted on the end shell 35. The support sleeve 37 of the steering device 32 is connected to the step wall 35a. The cover tube 36 of the soft resin is connected to a proximal surface of the end cap 30 to cover the support sleeve 37 and the proximal end of the end shell 35. The cover tube 36 constitutes an outer cover for the elongated tube 14 by covering the outer surface of the steering device 32 and extending to the handle device 15.

In FIG. 3, the distal surface 14a includes an imaging window area 40, lighting window areas 41 and 42 and the end nozzle 43 as well as the distal instrument opening 20. If required, other nozzles including a water jet nozzle are formed in the distal surface 14a. In FIG. 2, a channel sleeve 44 at a distal end is secured to the end shell 35 to communicate with the distal instrument opening 20. A sleeve having the instrument channel 19 is fitted externally on the proximal end of the channel sleeve 44. A mount hole 45 is formed in an inner position of the imaging window area 40. A lens barrel 52 of the solid state imaging unit 26 is mounted in the mount hole 45.

Figure 4:
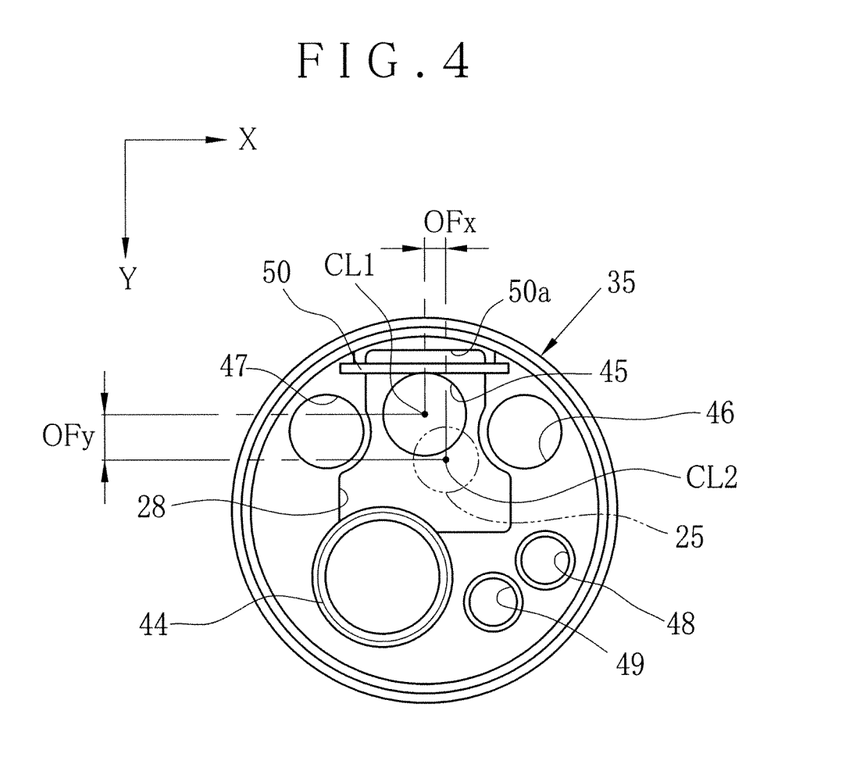
FIG. 4 is a front elevation illustrating an inner surface of an end shell.

In FIG. 4, light guide mount holes 46 and 47 are formed in the end shell 35 in addition to the mount hole 45 and the channel sleeve 44. The mount holes 46 and 47 are aligned with respectively the lighting window areas 41 and 42 of FIG. 3. The end shell 35 also includes flow channels 48 and 49 aligned with the end nozzle 43. A receiving opening 50 or coupling opening of a quadrilateral shape is formed in a portion higher than the mount hole 45. A holder opening 28 is formed in a portion lower than the receiving opening 50 and around the mount hole 45.

Figure 5:
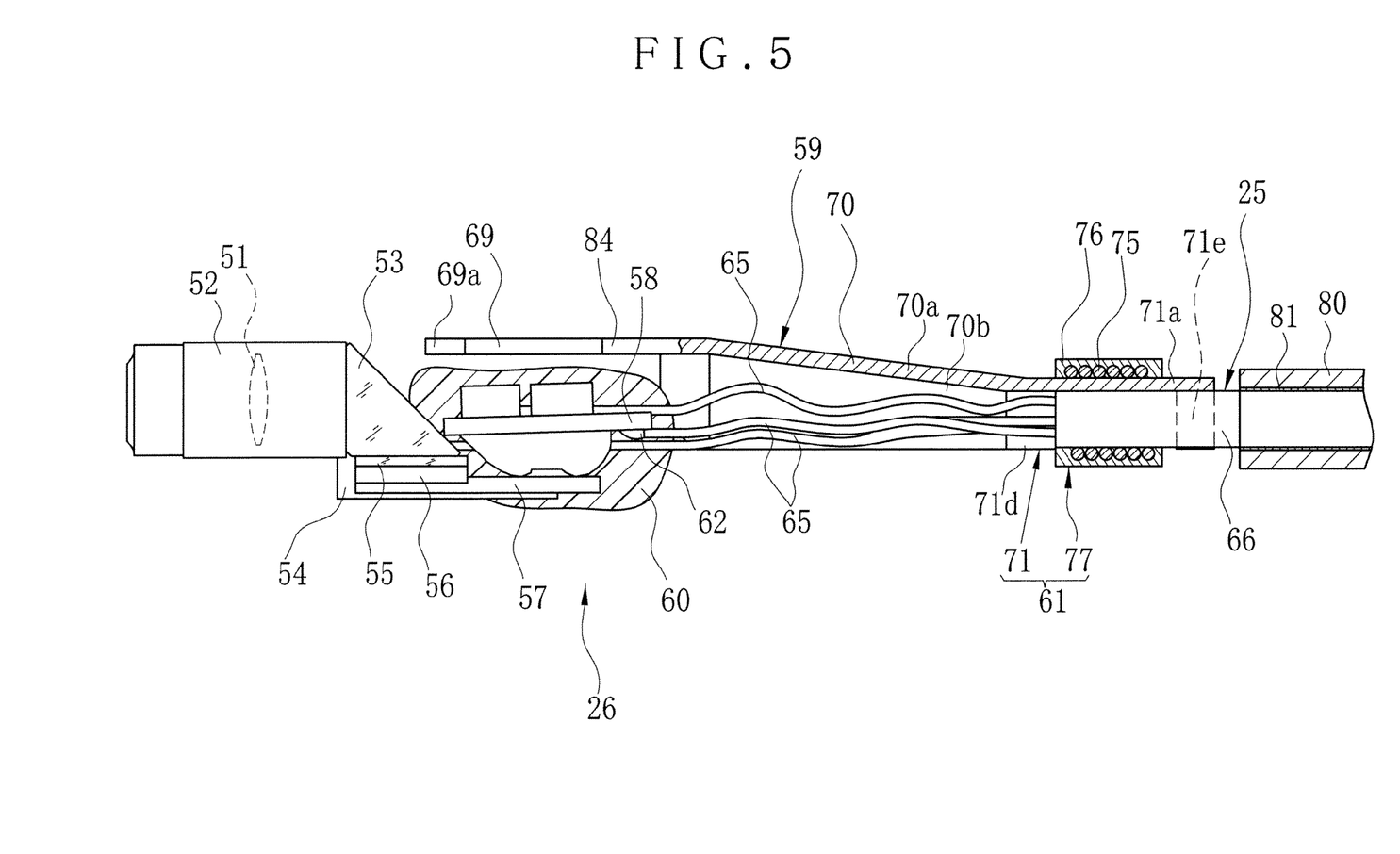
FIG. 5 is a vertical section illustrating a solid state imaging unit.

In FIG. 5, the solid state imaging unit 26 includes the lens barrel 52 and a prism 53, a prism holder 54, a cover glass 55, a CCD 56 as imaging device, a main circuit board 57, an additional circuit board 58, a cable holder 59 of a U shape, encapsulant 60 of resin, the signal cable 25, and a cable retaining device 61. An imaging lens 51 or lens system is mounted in the lens barrel 52, which is supported on the prism holder 54 together with the prism 53.

The CCD 56 is attached to the prism 53 with the cover glass 55. The CCD 56 is secured to the main circuit board 57, and converts image light focused by the imaging lens 51 and the prism 53 into a signal photoelectrically. A connection line (not shown) connects the main circuit board 57 to the additional circuit board 58. Circuit elements not mounted on the main circuit board 57 are mounted on the additional circuit board 58. The additional circuit board 58 is attached to the main circuit board 57 with adhesive agent. Note that the encapsulant 60 encapsulates the main circuit board 57, the additional circuit board 58, the prism 53 and the prism holder 54. A solder joint 62 is sealed by the encapsulant 60 between the boards and the filaments. It is possible to attach the additional circuit board 58 to the main circuit board 57 at the same time as the encapsulation with the encapsulant 60.

The signal cable 25 is a multi-filament cable, and includes a plurality of filaments 65, a shield line or shield layer (not shown) for bunching the filaments 65, and a cover material 66 or outer sheath for covering the filaments 65 and the shield layer. The filaments 65 and the shield layer are soldered to the main and additional circuit boards 57 and 58. Their length is sufficiently large so that their assemblage can be easy and stress of push or pull in the signal cable 25 is prevented from direct exertion to the filaments 65 or the solder joint 62. Note that the filaments 65, although connected to each one of the main and additional circuit boards 57 and 58, can be connected directly to only one of the main and additional circuit boards 57 and 58. Also, the additional circuit board 58 may consist of a flexible wiring board.

Figure 6:
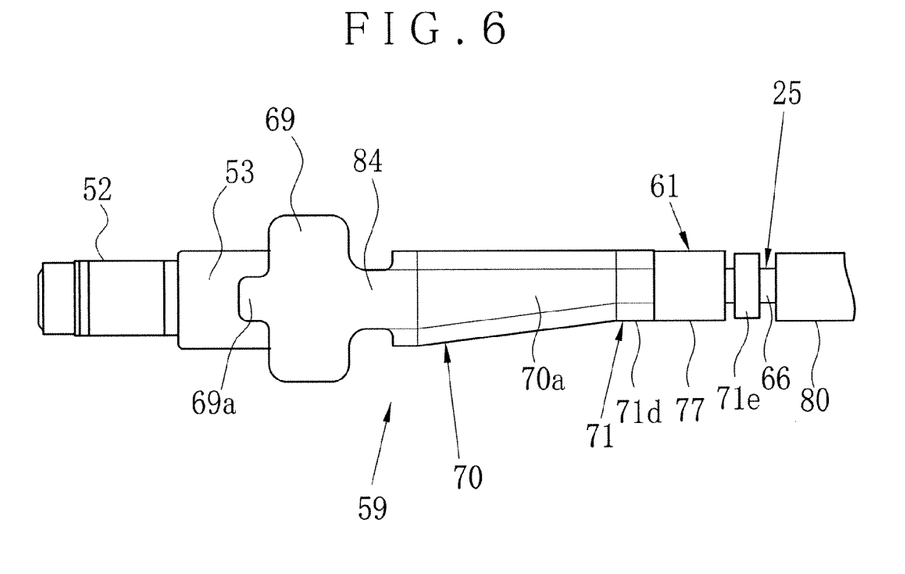
FIG. 6 is a plan illustrating the solid state imaging unit.
Figure 7:
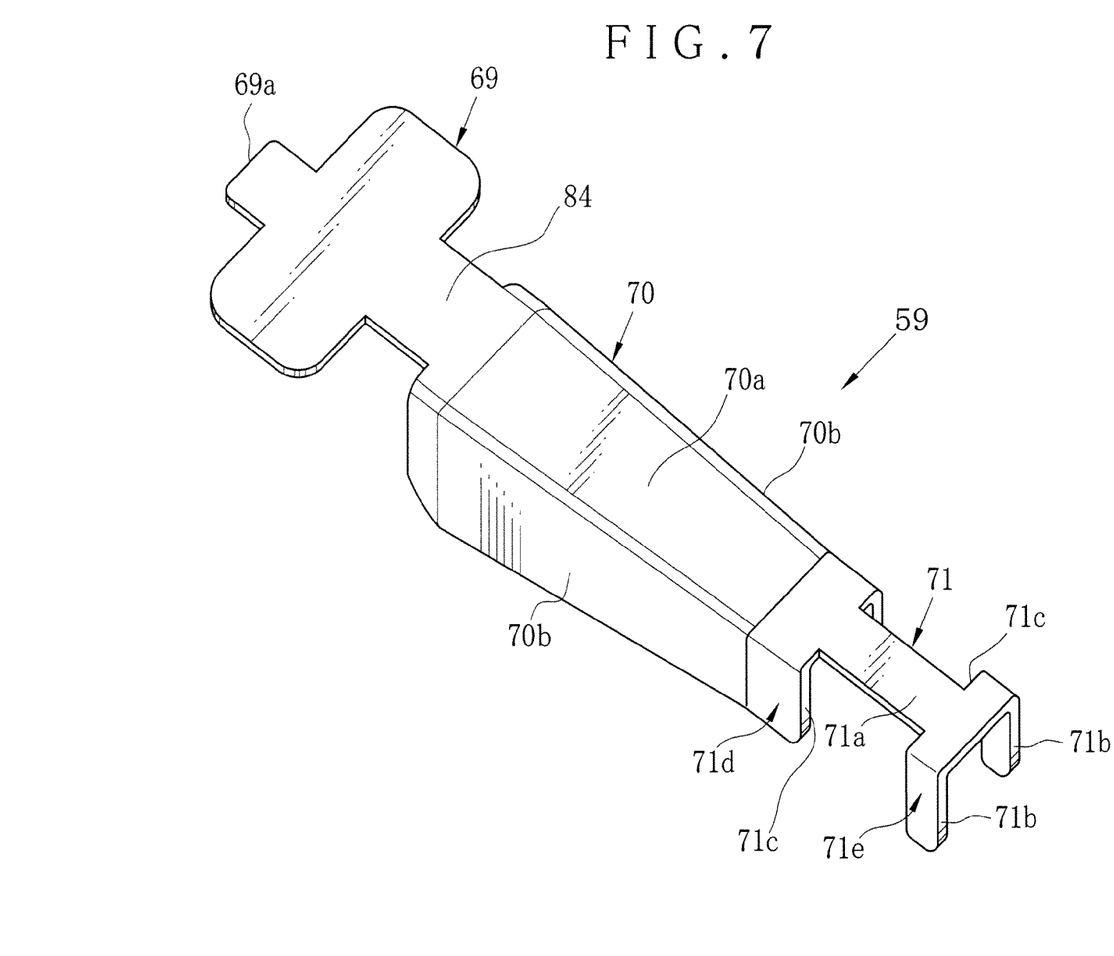
FIG. 7 is a perspective view illustrating a cable holder.

In FIGS. 6 and 7, the cable holder 59 includes a tip portion 69 or tongue portion, a cover device 70, and a cable retaining head 71 for anchoring arranged in a proximal direction. The tip portion 69 is a substantially quadrilateral plate. An anti-drop projection 69a is formed at a distal end of the tip portion 69.

Figure 8:
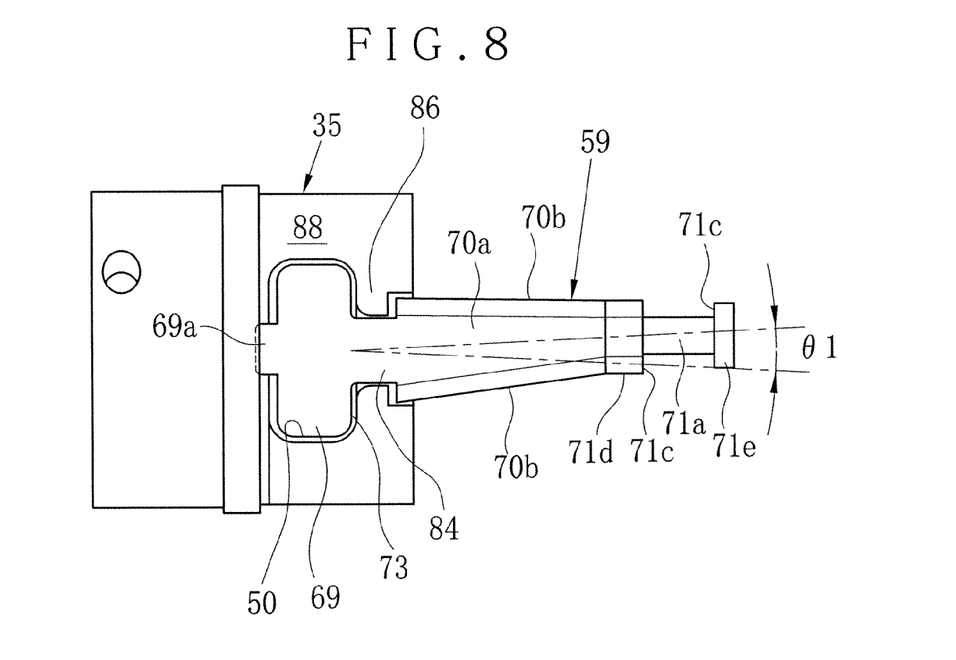
FIG. 8 is a plan illustrating a horizontal motion space in the end shell with the cable holder.

In FIG. 8, a state of securing the cable holder 59 to the end shell 35 is illustrated. The receiving opening 50 in an upper part of the end shell 35 is quadrilateral. A size of the receiving opening 50 is slightly larger than that of the tip portion 69. A horizontal motion space 73 is defined in a horizontal direction between the tip portion 69 and the receiving opening 50 according to their difference in the size. The tip portion 69 is pivotally movable in a horizontal direction within the range of the horizontal motion space 73. An angle θ1 of the horizontally pivotal movement is larger than m1 and smaller than m2, where m1 is an angle of a motion range due to the play of the first of the steering wheels (angle rings) in the horizontal direction, and m2 is an angle of a motion range free from the interference, according to calculation of a fill factor of contained elements in a section of the horizontal direction. Also, the angle θ1 is determined further in consideration of vertical motion of contained elements. Note that the horizontal motion angle due to play of the first steering wheel is originally very small because the first steering wheel is rotatable only in a vertical direction, but is referred to as an angle derived to the play at an extremely small value.

Figure 9:
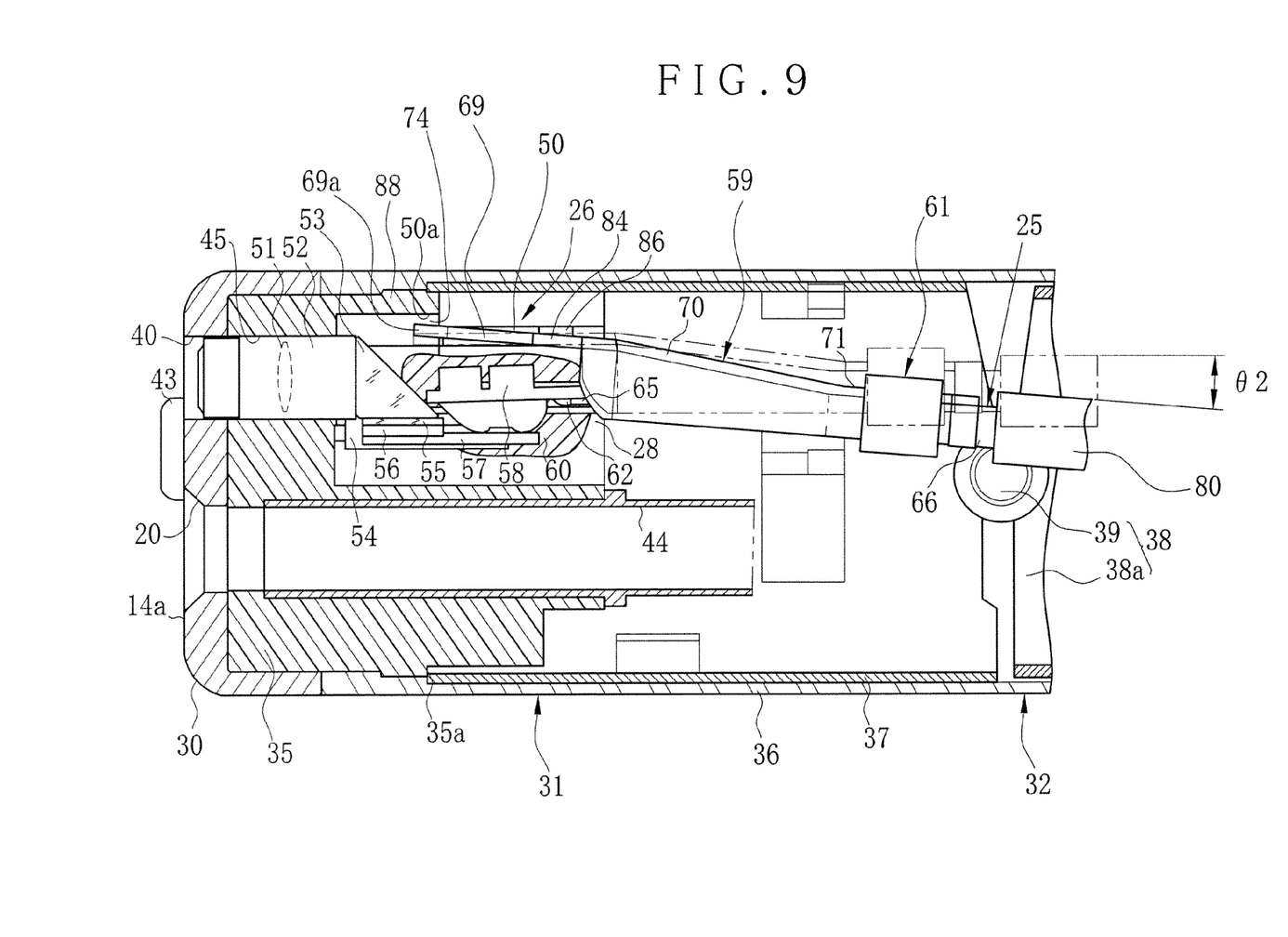
FIG. 9 is a vertical section illustrating a vertical motion space in the end shell with the cable holder.

In FIG. 9, a height of the receiving opening 50 is set larger than a thickness of the tip portion 69. A vertical motion space 74 is defined between the inside of the receiving opening 50 and the tip portion 69 in the vertical direction. The tip portion 69 is movable vertically in the receiving opening 50 within the vertical motion space 74. A moving angle θ2 of the tip portion 69 in the vertical direction is set larger than a1-a2, where a1 is an angular range where the first steering wheel is movable vertically, and a2 is a maximum angular range where the cable is movable. Also, the moving angle θ2 is determined by considering prevention of interference with peripheral parts or circuit elements.

The end shell 35 has a shell wall 88 disposed outside the tip portion 69 in a radial direction of the elongated tube 14. A neck section 84 is formed locally in the tip portion 69, and has a decreased width in a transverse direction of the tip portion 69. Receiving projections 86 as a coupling device project from edges of the receiving opening 50, are engaged with the neck section 84, and keep the tip portion 69 movable inside the receiving opening 50. The neck section 84 and the receiving projections 86 operate as coupling device for stress relief of stress generated in the signal cable 25.

A regulating surface 50a is an upper surface located at the receiving opening 50. When the cable holder 59 is entered in the receiving opening 50 of the end shell 35, the anti-drop projection 69a is regulated by the regulating surface 50a in order to prevent the tip portion 69 from dropping out of the receiving opening 50. Prevention of drop from the receiving opening 50 is specifically effective in provisional assembly of the cable holder 59 to the end shell 35 before securing the support sleeve 37 to the end shell 35. The assembling operation is easy. When the assembly is completed by fitting the support sleeve 37 around the end shell 35, the cable holder 59 is prevented from shifting vertically beyond its limit range, because regulated with the inner surface of the support sleeve 37. Thus, the tip portion 69 can be kept in the receiving opening 50 without drop. The cable holder 59 can be connected reliably to the end shell 35 both in a pivotally movable form and in a tightly connected manner without drop. Also, the filaments 65 with a sufficiently large length are used for connection with the main and additional circuit boards 57 and 58. Stress of push or pull in the signal cable 25 is not transmitted to the solder joint 62 of the filaments 65 or the main or additional circuit board 57 or 58.

Note that it is possible to adjust the interval between the anti-drop projection 69a and the regulating surface 50a by changing the bending angle of the anti-drop projection 69a. A range of pivotally moving the cable holder 59 can be finely adjusted.

In FIG. 7, the cover device 70 includes a center wall 70a and a pair of side walls 70b formed on the center wall 70a, and is in a U shape as viewed in a cross section (or in the axial direction). The filaments 65 are locally contained in the cover device 70. The cable holder 59 protects the filaments 65. The cover device 70 has a shape of which its cross-sectional area decreases in a proximal direction toward the cable retaining head 71. A ratio of the decrease in the cross-sectional area is irregular in the direction of the X axis, to determine the offset OFx on the X axis. See FIG. 4. In FIG. 5, there is a difference in the height between the tip portion 69 and the cable retaining device 61 with the cover device 70 in the direction of the Y axis, to determine the offset OFy on the Y axis.

In FIG. 4, the optical axis CL1 of the lens barrel 52 is offset from the center axis CL2 of the signal cable 25 because the lens barrel 52 and the cable holder 59 are secured to the end shell 35 with the offsets OFx and OFy. It is possible suitably to determine the offset OFx on the X axis and the offset OFy on the Y axis by changing the shape of the cover device 70. The signal cable 25 can be offset from the optical axis CL1 at any suitable points on a plane containing the X and Y axes. The signal cable 25 can be easily anchored on the cable retaining head 71 by the adhesion or caulking, because the cable retaining head 71 is formed by deforming the cover device 70 in a smaller form.

In FIG. 7, the cable retaining head 71 is formed in the same shape as a proximal end of the cover device 70 as viewed in a cross section. The cable retaining head 71 includes a center plate 71a or retaining wall, side walls 71b and a winding recess 71c. The winding recess 71c is formed in each of the side walls 71b. Segments of the side walls 71b are interconnected only by the center plate 71a. A first pair of side projections 71d on a distal side and a second pair of side projections 71e on a proximal side (anchoring projections) are constituted by the segments of the side walls 71b. The side projections 71d and 71e are caulked to squeeze the signal cable 25 laterally, firmly to anchor the cover material 66 of the signal cable 25 in FIG. 5.

In FIG. 5, a winding material 77 or drawstring is disposed between the side projections 71d and 71e, and includes winding turns 75 or strings, and sealant material 76 or adhesive agent. The winding turns 75 are wound about the center plate 71a of the cable retaining head 71 and the signal cable 25 which are kept in contact with one another. The cable retaining head 71 and the winding material 77 constitute the cable retaining device 61. Strength in connecting the signal cable 25 with the cable holder 59 is set high by the cable retaining device 61. Thus, the signal cable 25 can be kept on the cable holder 59 without offsetting even when the signal cable 25 is pushed or pulled by steering of the steering device 32 or when the cable retaining device 61 is shifted by the steering, because the strength of the connection is kept high by the squeeze of the winding material 77 with the side projections 71d and 71e. Occurrence of the peeling or breakage of the solder joint 62 from the filaments 65 can be prevented.

A protection sheath 80 covers the signal cable 25 near to a proximal end of the cable retaining device 61 and protects the signal cable 25 in the steering device 32. It is preferable to etch the cover material 66 at the distal end of the signal cable 25 and an inner surface of the protection sheath 80 at the distal end with etchant Tetra-Etch (trade name, manufactured by W. L. Gore & Associates, Inc.). A coating of adhesive agent 81 is applied by the etching with Tetra-Etch on the chemically active surface, so that the adhesion is strengthened. Note that a shield layer or shield line of the signal cable 25 is covered with a cover tube of a non-conductive property so as to prevent the contact with the cable holder 59.

In the embodiment, the protection sheath 80 is disposed at a proximal end of the cable retaining device 61. However, the protection sheath 80 can be extended to cover the cable retaining device 61 sufficiently. Stress of bending the signal cable 25 can be relieved with the protection sheath 80 upon steering of the steering device 32, because the cable retaining device 61 is partially covered with the protection sheath 80. Resistance against bending of the signal cable 25 can be set high.

The signal cable 25 can be so positioned as to minimize the influence of the degree of steering of the instrument channel 19 with the steering device 32 because the signal cable 25 is set opposite to the instrument channel 19 with respect to the diameter of the steering device 32 by use of the offsets OFx and OFy with the cover device 70. The signal cable 25 can be free from interference of the instrument channel 19. Durability of the signal cable 25 can be higher, to prevent irregularity in disposition of the signal cable 25 and tubular elements within the steering device 32. Breakage of the signal cable 25 can be suppressed by reducing mechanical damage.

As the signal cable 25 is secured to the end shell 35 by use of the cable holder 59, breakage of the filaments 65 and removal of the solder joint 62 can be prevented. This is because the filaments 65, the solder joint 62 and the main and additional circuit boards 57 and 58 are free from stress created by steering of the steering device 32 to bend or push and pull the signal cable 25.

The tip portion 69 at the end of the cable holder 59 is inserted in the receiving opening 50 to define the motion spaces 73 and 74 between the receiving opening 50 and the tip portion 69. It is possible to keep the cable holder 59 movable pivotally with the end shell 35, in as large a range as 50% in the directions of the X and Y axes. Even when stress of bending or push or pull is generated in the signal cable 25, the cable holder 59 moves pivotally in the range of the motion spaces 73 and 74. Durability of the signal cable 25 can be increased because the stress can be reduced.

In the embodiment, the solid state imaging unit 26 can be structured compactly because of local division of the main and additional circuit boards 57 and 58, to reduce the diameter and length of the head assembly 31. The prism holder 54 holds the prism 53 between the lens barrel 52 and the CCD 56. The additional circuit board 58 is disposed at a proximal end of the prism 53. Thus, a space next to the prism 53 on the proximal side can be utilized effectively. The diameter of the head assembly 31 can be reduced. The water impermeability of the construction can be ensured by combining the prism 53 and the main and additional circuit boards 57 and 58 as a unit, and sealing the solder joint 62 with the encapsulant 60 on the filaments 65 of the main and additional circuit boards 57 and 58.

A method of assembling parts of the head assembly 31 is described now. At first, the cover material 66 of the signal cable 25 is inserted in the cable retaining head 71 of the cable holder 59, and unified by winding the winding turns 75 and applying the sealant material 76, so as to obtain the cable retaining device 61. Thus, the signal cable 25 is firmly anchored to the cable holder 59. The side projections 71d and 71e are caulked by use of a crimp tool or nippers, and are fitted on the cover material 66 tightly.

Then various elements are mounted on the prism holder 54, including the lens barrel 52, the prism 53, the cover glass 55, the CCD 56, and the main and additional circuit boards 57 and 58. The filaments 65 of the signal cable 25 are connected to the main and additional circuit boards 57 and 58 by use of solder material. The filaments 65 are sufficiently loosened with a considerable length while extended through the cover device 70.

Then the prism 53, the prism holder 54, and the main and additional circuit boards 57 and 58 including the solder joint 62 are encapsulated with the encapsulant 60. Thus, the solid state imaging unit 26 having the signal cable 25 together with the cable holder 59 is obtained.

The solid state imaging unit 26 is secured to the end shell 35. At first, the tip portion 69 of the cable holder 59 is inserted in the receiving opening 50 of the end shell 35. Then the support sleeve 37 of the steering device 32 is set on the peripheral surface of the end shell 35. Thus, the support sleeve 37 covers the receiving opening 50. The cable holder 59 is regulated with the inner surface of the support sleeve 37, so as to prevent the tip portion 69 from excessively moving within a safely positioned range at the receiving opening 50. The cable holder 59 is connected in a pivotally movable manner to the end shell 35 by use of the tip portion 69 and the receiving opening 50. Then the end cap 30 and the cover tube 36 are fitted on the end shell 35 and the steering device 32 to complete the securing operation. As a result, it is possible to secure the signal cable 25 to the end shell 35 easily by entry of the tip portion 69 in the receiving opening 50. The solid state imaging unit 26 can be secured to the head assembly 31 easily.

In operation, the steering wheels 21 of the handle device 15 are rotated to pull the support sleeve 37 by use of the wires 34 arranged in an angularly equidistant manner, to steer the steering device 32 in a desired direction at a desired angle. The signal cable 25 is moved in the proximal or distal direction upon the steering. In response, the cable holder 59 is moved pivotally with the motion spaces 73 and 74 defined by the receiving opening 50 and the tip portion 69 or tongue portion, to reduce the stress of the push or pull. The signal cable 25 is bent at an end of the cable retaining device 61. The stress of the bend is also reduced by the pivotal movement of the cable holder 59 and the end shell 35. Thus, it is possible to prevent breakage of the signal cable 25 due to the stress. The stress is exerted to the end shell 35 by the cable holder 59 and not exerted to the solder joint 62 or the main or additional circuit board 57 or 58. This is effective in preventing breakage of the filaments 65 or damage of the solder joint 62 due to steering of the steering device 32.

In the above embodiments, the tip portion 69 and the receiving opening 50 are quadrilateral. However, a tip portion or tongue portion and a receiving opening can be formed in other shapes, such as triangular, semi-circular, semi-elliptical, circular, or elliptical shapes. In the above embodiments, the tip portion is in the plate shape. However, the tip portion can be formed in other shapes such as a shaft shape and spherical shape, for the purpose of allowing pivotal movement of the cable retaining head finely in horizontal and vertical direction. In the above embodiments, the receiving structure for stress relief is the receiving opening. However, the receiving structure or coupling device can be formed in other shapes such as a projection and retaining pin, for the purpose of keeping the retaining portion pivotally movable.

Note that the end shell 35, although formed in the cylindrical sleeve shape, may be formed in a box shape, frame shape, disk shape and the like.

In the above embodiment, the first and second pairs of the side projections 71d and 71e are included in the cable retaining head 71. However, only the first or second pair of the side projections 71d or 71e may be formed for anchoring.

The sealant material 76 or adhesive agent can be omitted for anchoring. The signal cable 25 can be anchored to the cable holder 59 only by the winding turns 75 without use of the side projections 71d and 71e, and also only by the side projections 71d and 71e without use of the winding turns 75.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An endoscope having a section of an elongated tube for entry in a body cavity, comprising:
   an end shell disposed at a distal end of said elongated tube;
   an imaging window area formed in said end shell;
   a lens barrel, secured to said end shell, and aligned with said imaging window area;
   an imaging device for photoelectrically converting object light from said lens barrel;

a circuit board having said imaging device mounted thereon;

a signal cable, having plural filaments for transmitting at least an image signal from said imaging device, and a cover material for covering said filaments;

a cable holder, including a cable retaining device and a tip portion, said cable retaining device partially anchoring said cover material of said signal cable, said tip portion being disposed on a distal side of said cable retaining device;

a coupling device for keeping said tip portion laterally movable on said end shell, to prevent stress in said cable retaining device from exertion to said end shell;

a mount hole formed through said end shell, for contacting and receiving said lens barrel therein, wherein said tip portion is in a plate shape;

a shell wall, formed with said end shell, and disposed outside said tip portion;

a receiving opening, formed in said shell wall, for receiving said tip portion; and a neck section formed locally with said tip portion with a decreased width, wherein said coupling device includes a receiving projection, disposed to project from said receiving opening, engaged with said neck section, for keeping said tip portion movable inside said receiving opening.

2. An endoscope as defined in claim 1, wherein said receiving opening has a larger size than a size of said tip portion.

3. An endoscope as defined in claim 2, wherein said receiving opening has a larger thickness than a thickness of said tip portion.

4. An endoscope as defined in claim 3, wherein said receiving opening includes a regulating surface for receiving an end of said tip portion upon lateral movement of said cable holder.

5. An endoscope as defined in claim 3, further comprising a support sleeve for supporting said end shell at a distal end thereof, and covering said receiving opening.

6. An endoscope as defined in claim 1, further comprising a prism for directing said object light from said lens barrel to said imaging device.

7. An endoscope as defined in claim 6, further comprising an additional circuit board, having a circuit element mounted thereon, disposed on a proximal side from said prism, and connected with said circuit board and with said filaments of said signal cable.

8. An endoscope as defined in claim 7, wherein said additional circuit board is at least partially opposed to a wall of said tip portion.

9. An endoscope as defined in claim 1, wherein said cable holder further includes a cover device, disposed to extend in an axial direction between said cable retaining device and said tip portion, for partially containing said filaments.

10. An endoscope as defined in claim 9, wherein said cover device includes:

a center wall; and side walls disposed to project from edges of said center wall in a channel shape.

11. An endoscope as defined in claim 10, wherein a first one of said side walls is inclined to decrease a distance to a second one thereof, and offsets an axis of said signal cable from an optical axis of said lens barrel in said end shell.

12. An endoscope as defined in claim 1, wherein said cable retaining device includes:

a center plate having a small width; and first and second pairs of projections disposed respectively in a channel shape, said first pair being disposed on a distal side of said center plate, said second pair being disposed on a proximal side of said center plate.

13. An endoscope as defined in claim 12, further comprising:

a winding material wound around said center plate and said cover material of said signal cable; and a sealant material disposed around said winding material.

* * * * *